United States Patent [19]

Di Meo

[11] Patent Number: 5,087,565
[45] Date of Patent: Feb. 11, 1992

[54] SYNTHETIC PROCESS FOR PREPARATION OF $^{32}$P-LABELED NUCLEOTIDES

[75] Inventor: James J. Di Meo, Watertown, Mass.

[73] Assignee: Du Pont Merck Pharmaceutical Company, Wilmington, Del.

[21] Appl. No.: 627,866

[22] Filed: Jul. 2, 1984

[51] Int. Cl.$^5$ .................. C12P 19/30; C07H 15/12; C07H 17/00
[52] U.S. Cl. ....................... 435/89; 536/27; 536/28
[58] Field of Search ............ 435/89, 90, 140, 194, 435/131; 536/27, 28

[56] References Cited

U.S. PATENT DOCUMENTS 4,209,589 6/1980 Johnson et al. .............. 435/90
4,554,253 11/1985 Imahori et al. ............... 435/89

OTHER PUBLICATIONS

Maher et al., "Basic Biological Chemistry", Harper & Row, pp. 275 and 318–319, (1968).
Lehnenger, A. L., "Biochemistry", 2nd Ed., (1976), Worth Publ. Inc., pp. 547–548.
Bauer et al., (1978), Analytical Biochemistry, vol. 81, pp. 613–617.

Primary Examiner—Elizabeth C. Weimer
Assistant Examiner—Gail Poulos
Attorney, Agent, or Firm—Gildo E. Fato

[57] ABSTRACT

A process for the production of $^{32}$P-labeled nucleotides in accordance with an enzymatic pathway utilizing phosphotransacetylase and acetate kinase.

10 Claims, No Drawings

SYNTHETIC PROCESS FOR PREPARATION OF $^{32}$P-LABELED NUCLEOTIDES

BACKGROUND $^{32}$P-labeled nucleotides are used routinely for radioactive labeling of DNA and RNA, usually for nucleic acid sequencing and recombinant DNA/RNA research.

Until about 1979, the method generally used for synthesis of radiolabeled nucleotides was via the process disclosed by Schendel and Wells (J. Biol. Chem. 248, 8319-8321 (1973)) which introduced $^{32}$P into one of many well known metabolic pathways as follows:

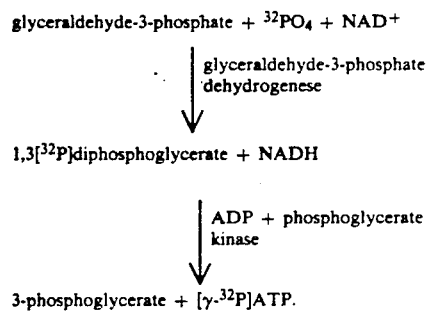

1,3[$^{32}$P]diphosphoglycerate + NADH $$\downarrow \text{ADP + phosphoglycerate kinase}$$

3-phosphoglycerate + [$\gamma$-$^{32}$P]ATP.

This pathway, however, does not produce carrier-free nucleotides because the starting material glyceraldehyde-3-phosphate (GAP) is somewhat unstable and hence breaks down to liberate free nonradioactive phosphate, resulting in an apparent specific activity of 4000–6000 Ci/m mole, about half of the theoretical carrier-free specific activity of 9140 Ci/m mole.

To overcome the stability problems associated with utilizing GAP as a starting material, Johnson and Walseth disclosed in U.S. Pat. No. 4,209,589 the concept of generating GAP in situ by tracing backwards in the same metabolic pathway to the starting material glycerophosphate, such process represented by the following pathway:

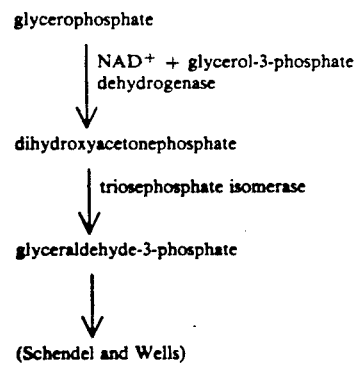

(Schendel and Wells)

The Johnson and Walseth method, however, generally only produces [$\gamma$-$^{32}$P-labeled] nucleotides having specific activities of from about 4500-6500 Ci/m mole because the enzymes used in the process are only available containing varying amounts of impurities; and purification techniques for these enzymes are quite tedious.

It would be useful, therefore, to devise a simple enzymatic method, preferably one not requiring tedious purification steps, for producing radiolabeled nucleotides that have specific activities approaching theoretical carrier-free levels in order to increase the apparent sensitivity of assays which employ such radiolabeled nucleotides.

SUMMARY

The subject invention is a process for the synthesis of $^{32}$P-labeled nucleotides in accordance with the following enzymatic route:

1. $H_3{}^{32}PO_4$ + acetyl-CoA

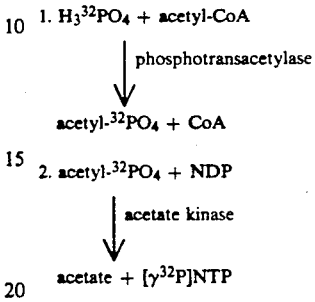

acetyl-$^{32}PO_4$ + CoA 2. acetyl-$^{32}PO_4$ + NDP $$\downarrow \text{acetate kinase}$$

acetate + [$\gamma{}^{32}$P]NTP where NDP is any of the well known nucleoside diphosphates, NTP is any of the corresponding gamma-radiolabeled nucleoside triphosphates, and where acetyl-CoA can alternatively be proprionyl-CoA, butyryl-CoA.

DETAILED DESCRIPTION

In the reaction scheme outlined above for production of radiolabeled NTP, the NDP used can be any of the well known nucleoside diphosphates, preferably adenosine 5'diphosphate (ADP), guanosine 5'-diphosphate (GDP), cytidine 5'-diphosphate (CDP), uridine 5'-diphosphate (UDP), 2'-deoxyadenosine 5'-diphosphate (dADP), 2'-deoxyguanosine 5'-diphosphate (dGDP), 2'-deoxycytidine 5'-diphosphate (dCDP), 2'-deoythymidine 5'-diphosphate (dTDP), inosine 5'-diphosphate (IDP), and 8-azido adenosine 5'-diphosphate (8-azido-ADP), all such diphosphates being substrates for E. coli acetate kinase. ADP is presently preferred in the practice of the subject invention. Of course, the corresponding gamma-radiolabeled nucleotide triphosphates are, respectively ATP, GTP, CTP, UTP, dATP, dGTP, dCTP, dTTP, ITP and 8-azido-ATP.

The well known coenzyme acetyl-CoA is readily available from e.g. Sigma Corp. of St. Louis, Boehringer-Mannheim Inc. of Mannheim, W. Germany, or Pharmacia PL Biochemicals of Milwaukee, Wisconsin, all of which can be used without further purification. Although acetyl-CoA is preferred, especially when phosphotransacetylase from Clostridium kluyveri is used, other CoA derivatives can be employed such as proprionyl-CoA, butyryl-CoA or succinyl-CoA.

Acetate kinase from E. Coli is preferred in the practice of the subject invention, although acetate kinase from other organisms can also be used, such as from Bacillus stearothermophilus, Veillonella alcalescens, Proteus vulgaris, Clostridium, Streptococcus haemolytics and Azotobacter vinelandii. Certain of these various kinases are also available commercially from Sigma, Boehringer, and Pharmacia PL Biochemicals. These kinases may be purified by conventional procedures to remove traces of inorganic phosphates, and other contaminating entities such as ATPase, GTPase and phosphatases, however, the process of the subject invention does not require such purification.

Sources of phosphotransacetylase include Clostridium kluyveri, Clostridium thermoaceticum, Salmonella

*typhimurium, E. Coli.*, myobacteria, treponemes, *Bacillus subtilis, Aerobacter aerogenes, Clostridium acidurici, Veillonella alcalescens, Lactobacillus fermenti* and *Streptococcus faecalis*. Phosphotransacetylase is also available commercially from Sigma, Boehringer and Pharmacia PL.

The above-detailed reaction is carried out at a pH of about 6-9, preferably 7.5 to 8. In this regard, buffer systems such as Tris-HCI, glycylglycine, histidine or triethanolamine are useful to maintain appropriate pH for the reaction. Reaction temperatures in the range of 15°-25° C. are preferred although a wider temperature range would be acceptable so long as extreme temperatures which would deactivate the enzymes are avoided. Acceptable product formation (>80% yield) occurs in about 5-10 minutes, but the reaction can be allowed to proceed until complete. However, after about 15 minutes, the reaction should be closely monitored using the PEI-Cellulose TLC strip method described below and stopped before excess hydrolysis occurs of the γ-phosphate from phosphotase or nucleotidase contaminants within the phosphotransacetylase or acetate kinase.

Phosphotransacetylase requires the presence of a monovalent cation, e.g. $K^+$ or $NH_4^+$ and acetate kinase requires the presence of a divalent cation, e.g. $Mg^{++}$, $Mn^{++}$, $Co^{++}$, $Zn^{++}$ or $Cd^{++}$. Also, both enzymes require a reducing agent to prevent inactivation by sulfhydryl group oxidation using DTT, mercaptoethanol, cysteine, glutathione or dimercaptopropanol.

The activity of the enzymes can be anywhere from about 25 to 100 units/ml for phosphotransacetylase, and 6-25 U/ml for acetate kinase.

EXAMPLE

The reaction was carried out with lead shielding at room temperature. In general, the quantity of reaction ingredients is a function of the initial volume of $^{32}P$-orthophosphate ($H_3\ ^{32}PO_4$) used. The following components were added to the reaction mixture for every 100 microliters of $H_3\ ^{32}PO_4$ (carrier-free in 0.02N HCI, concentration about 80 μM): 10 microliters 1M Tris-HCI, pH9; 2 microliters 0.1M $MgCl_2$; 51 microliters $H_2O$; 2 microliters 0.1M DTT; 2 microliters 10 mM ADP; 20 microliters 20 mM acetyl-CoA; 10 microliters phosphotransacetylase at 1 units/ml in 50 mM Tris-HCI, pH 7.8, 200 mM ammonium sulfate and 2 mM DTT; and 10 microliters acetate kinase at 0.25 units/μL in the same buffer as the phosphotransacetylase. Scale-up of these volumes should be done linearly depending on the volume of $H_3\ ^{32}PO_4$ used.

The reaction was initiated by addition of the tris buffer, $MgCl_2$, $H_2O$ and DTT to the $H_3\ ^{32}PO_4$. The reactants were mixed carefully and ADP and acetyl-CoA added, followed by addition of the two enzymes. The order of addition is not critical, but the enzymes should be added last.

Aliquots were taken at 5 minute intervals and spotted on PEI-Cellulose TLC strips which were developed with 0.6M ammonium formate (pH 3.5). The status of the reaction was monitored via both autoradiography on X-ray film and Geiger-Muller scanning of the PEI-Cellulose strips ($R_f$ATP=0, $R_f$phosphate=0.6).

Upon completion (yield >80%), the reaction was be stopped vial addition of 10 microliters 1N HCI. The specific activity of the resulting [$\gamma^{32}P$] ATP was greater than about 7500 Ci/mmol.

I claim:

1. A process for the production of $^{32}P$-labeled NTP comprising (i) reacting $H_3\ ^{32}PO_4$ with an excess of X-CoA where X is selected from the group consisting of acetyl, propionyl, butyryl and succinyl in the presence of phosphotransacetylase, inducing the formation of $^{32}PO_4$-labeled X, (ii) simultaneously reacting the resulting X-$^{32}PO_4$, as it is formed, with NDP in the presence of acetate kinase, under conditions capable of both inducing the formation of X-$^{32}PO_4$ and conversion of NDP to $^{32}P$-labeled NTP, and (iii) stopping the reactions before excess hydrolysis of $^{32}P$-labeled NTP occurs to prepare said product having a specific activity greater than 7500 Ci/mM.

2. The process of claim 1 where X is acetyl.

3. The process of claim 1 or 2 where NDP is selected from the group consisting of ADP, GDP, CDP, UDP, dADP, dGDP, dCDP, dTDP, IDP and 8-azido-ADP, and NTP is the corresponding nucleotide triphosphate.

4. The process of claim 3 where NDP is ADP and NTP is ATP.

5. A process for the production of $^{32}P$-labeled NTP comprising (i) reacting $H_3\ ^{32}PO_4$ with an excess of acetyl-CoA in the presence of phosphotransacetylase and a monovalent cation to allow formation of acetyl-$^{32}PO_4$, (ii) simultaneously reacting acetyl-$^{32}PO_4$, as it is formed, with NDP in the presence of acetate kinase and a divalent cation under reaction conditions sufficient to both allow formation of acetyl-$^{32}PO_4$ and to allow formation of ($^{32}PO_4$)NTP, and (iii) stopping the reactions before excess hydrolysis of ($^{32}PO_4$) NTP takes the yield below 80% to prepare said product having a specific activity greater than 7500 Ci/mM.

6. The process of claim 5 where the monovalent cation is selected from $K^+$, and $NH_4^+$ and the divalent cation is selected from $Mg^{++}$, $Mn^{++}$, $Co^{++}$, $Zn^{++}$ and $Cd^{++}$.

7. The process of claim 5 or 6 where NDP is selected from the group consisting of ADP, GDP, CDP, UDP, dADP, dGDP, dCDP, dTDP, IDP and 8-azido-ADP, and NTP is the corresponding nucleotide triphosphate.

8. The process of claim 7 where NDP is ADP and NTP is ATP.

9. A gamma-$^{32}P$-labeled nucleotide triphosphate having a specific activity greater than 7500 Ci/mM.

10. The gamma-$^{32}P$-labeled nucleotide triphosphate of claim 9 which is $^{32}P$-adenosine triphosphate.

* * * * *